United States Patent
Oguzman et al.

(10) Patent No.: US 9,157,897 B2
(45) Date of Patent: Oct. 13, 2015

(54) HIGH VOLTAGE ULTRASOUND TRANSMITTER WITH GATE PROTECTION DIODES AND INTRINSIC OUTPUT ZEROING

(75) Inventors: Ismail H. Oguzman, Plano, TX (US); Arash Loloee, Allen, TX (US); Suribhotla Rajasekhar, Plano, TX (US); Karthik Vasanth, Richardson, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 888 days.

(21) Appl. No.: 12/582,752

(22) Filed: Oct. 21, 2009

(65) Prior Publication Data

US 2011/0088475 A1    Apr. 21, 2011

(51) Int. Cl.
| | | |
|---|---|---|
| A61B 8/00 | (2006.01) | |
| G01N 29/32 | (2006.01) | |
| B06B 1/02 | (2006.01) | |
| G01N 29/06 | (2006.01) | |
| G01N 29/34 | (2006.01) | |

(52) U.S. Cl.
CPC ............ *G01N 29/32* (2013.01); *B06B 1/023* (2013.01); *G01N 29/06* (2013.01); *G01N 29/34* (2013.01)

(58) Field of Classification Search
USPC ....... 73/632; 307/106; 326/68; 327/106, 108, 327/112, 276, 295, 350, 538; 345/204; 361/58; 363/132; 365/189.11; 600/437, 600/443
See application file for complete search history.

(56) References Cited

U.S. PATENT DOCUMENTS

| | | | | |
|---|---|---|---|---|
| 5,729,418 A * | 3/1998 | Lei | ................................... | 361/58 |
| 5,909,134 A * | 6/1999 | Sohn et al. | .................... | 327/295 |
| 6,549,052 B2 * | 4/2003 | Okayasu | ........................ | 327/276 |
| 7,480,191 B2 * | 1/2009 | Walker et al. | ............. | 365/189.11 |
| 7,538,581 B2 * | 5/2009 | Walker | ............................. | 326/68 |
| 7,564,263 B2 * | 7/2009 | Walker et al. | .................... | 326/63 |
| 7,659,756 B2 * | 2/2010 | Walker | ........................... | 327/112 |
| 7,893,714 B2 * | 2/2011 | Chu | ................................. | 326/68 |
| 7,956,653 B1 * | 6/2011 | Choy et al. | ..................... | 327/108 |
| 7,977,820 B2 * | 7/2011 | Chu et al. | ........................ | 307/106 |
| 8,013,640 B1 * | 9/2011 | Chu | ................................ | 327/106 |
| 8,154,898 B2 * | 4/2012 | Walker | ........................... | 363/132 |
| 2006/0186944 A1 * | 8/2006 | Chan et al. | ..................... | 327/350 |
| 2006/0238527 A1 * | 10/2006 | Walker et al. | ................. | 345/204 |
| 2007/0069771 A1 * | 3/2007 | Walker | ........................... | 327/112 |
| 2007/0126493 A1 * | 6/2007 | Ko et al. | ........................ | 327/538 |

(Continued)

OTHER PUBLICATIONS

MD1810, High Speed Quad Mosfet Driver, Supertex, Sep. 1, 2005.*

(Continued)

*Primary Examiner* — Unsu Jung
*Assistant Examiner* — Serkan Akar
(74) *Attorney, Agent, or Firm* — Alan A. R. Cooper; Frank D. Cimino

(57) ABSTRACT

An ultrasound transmitter including intrinsic output zeroing is disclosed herein. A transmitter for generating ultrasound signals includes a first transmitter output driver and a first transmitter input driver. The first transmitter output driver includes an N-type device serially coupled to a P-type device. The first transmitter input driver includes an N-type device serially coupled to a P-type device. An output of the first transmitter input driver is coupled to an input of the first transmitter output driver. The first transmitter output driver drives an output of the transmitter to a first voltage and the first transmitter input driver drives the output of the transmitter to a second voltage while the first transmitter output driver is disabled.

14 Claims, 3 Drawing Sheets

(56) References Cited

U.S. PATENT DOCUMENTS

2008/0242987 A1* 10/2008 Shifrin .......................... 600/443
2011/0088475 A1* 4/2011 Oguzman et al. ............... 73/632
2012/0108963 A1* 5/2012 Hara et al. .................... 600/437

OTHER PUBLICATIONS

MD1711, High Speed Integrated US Driver IC, Supertex, Mar. 26, 2007.*

* cited by examiner

HIGH VOLTAGE ULTRASOUND TRANSMITTER WITH GATE PROTECTION DIODES AND INTRINSIC OUTPUT ZEROING

BACKGROUND

Ultrasonic imaging has become a widely used tool in medical applications. Ultrasound techniques introduce high-frequency acoustic waves into a subject's body. The received echoes of those waves provide information allowing a trained observer to view the subject's internal organs. Ultrasound imaging equipment uses transducers that convert electrical energy into acoustic energy. Piezo-electric crystals are one commonly used type of electrical to acoustical transducer. To obtain a clear image, a high signal to noise ratio is desirable to overcome random noise associated with the imaging process. One way to increase the signal-to-noise ratio is to increase the amplitude of the signal driving the transducer. Generally, the transducer drive signal may require voltages in the range of +/−75 volts to +/−100 volts.

There are two broad categories of ultrasound transmitters, digital and analog. The analog type takes a signal generated digitally and after being converted to analog form, by a digital-to-analog converter, the signal is amplified to the required higher voltage by a power amplifier. This type of transmitter is capable of generating complex waveforms by using a high-resolution digital-to-analog converter with a resolution of, for example, 12 bits. This technique is expensive and finds application in high-end ultrasound imaging systems. Digital transmitters are simpler and less expensive than analog transmitters.

SUMMARY

An ultrasound transmitter including intrinsic output zeroing is disclosed herein. In accordance with some embodiments, a transmitter for generating ultrasound signals includes a first transmitter output driver and a first transmitter input driver. The first transmitter output driver includes an N-type device serially coupled to a P-type device. The first transmitter input driver includes an N-type device serially coupled to a P-type device. An output of the first transmitter input driver is coupled to an input of the first transmitter output driver. The first transmitter output driver drives an output of the transmitter to a first voltage, and the first transmitter input driver drives the output of the transmitter to a second voltage while the first transmitter output driver is disabled.

In accordance with at least some other embodiments, a method includes concurrently disabling each of a plurality of output driver circuits of a transmitter. A low-impedance path is formed, responsive to the disabling, between an output of the transmitter and an output of an input driver circuit configured to selectively enable and disable at least one of the output driver circuits.

In accordance with yet other embodiments, an ultrasound imaging system includes an ultrasonic signal transducer and a signal transmitter. The ultrasonic signal transducer converts an electrical signal into an acoustical signal. The signal transmitter is coupled to the ultrasonic transducer. The signal transmitter includes a high-side output driver and a high-side input driver. The high-side output driver drives a transmitter output to a first non-zero voltage when enabled. The high-side input driver has an output coupled to control inputs of the high-side output driver. The high-side input driver is configured to selectively enable and disable the high-side output driver. The high-side output driver, when disabled, provides a low-impedance path from the transmitter output to the high-side input driver. Embodiments may also include a low-side output driver and a low-side input driver. When enabled, the low-side output driver drives the transmitter output to a second non-zero voltage. The low-side input driver has an output coupled to control inputs of the low-side output driver, and is configured to selectively enable and disable the low-side output driver. When disabled, the low-side output driver provides a low-impedance path from the transmitter output to the low-side input driver.

BRIEF DESCRIPTION OF THE DRAWINGS

For a detailed description of exemplary embodiments of the invention, reference will now be made to the accompanying drawings in which.

NOTATION AND NOMENCLATURE

Figure 1:
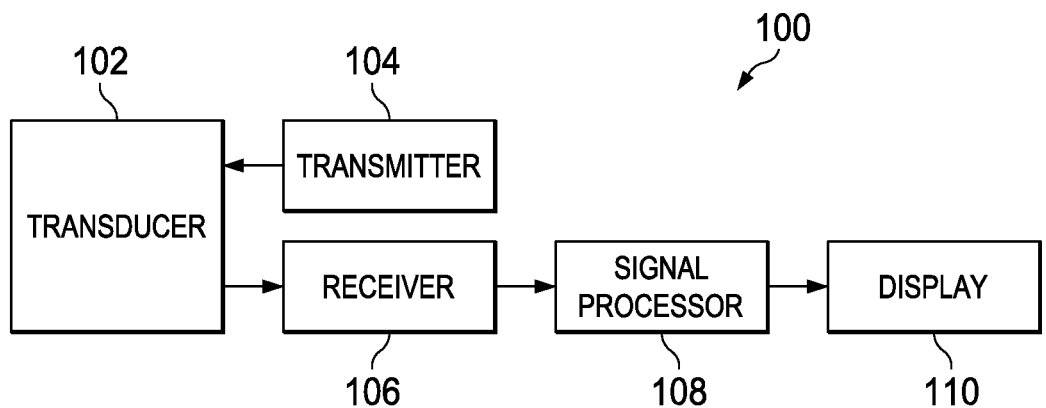
FIG. 1 shows a block diagram of an exemplary ultrasound imaging system in accordance with various embodiments.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . . " Also, the term "couple" or "couples" is intended to mean either an indirect or direct electrical connection. Thus, if a first device couples to a second device, that connection may be through a direct electrical connection, or through an indirect electrical connection via other devices and connections.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

An embodiment of a digital ultrasound transmitter includes a push-pull transistor arrangement whereby a first drive transistor drives the transmitter output to a positive high voltage, and a second drive transistor drives the transmitter output to a negative high voltage. Such transmitters generally produce three signal levels "high," "low," and "zero." The "zero" signal level cannot be produced by the push-pull structure alone. The "return-to-zero" or "damping" function can be produced via an external load, a bleeding resistor, or a dedicated active damping circuit, any of which may be included to discharge the transmitter output when both push and pull transistors are disabled.

Discharging through the load is undesirable because the load can vary across applications resulting in differing and often unacceptably high "settling times" (i.e., the time required for the transmitter output to return to zero). Discharge through a damping resistor is also problematic because fast settling time (e.g., 100 nanoseconds) cannot be obtained with a typical value of damping resistance (e.g., 10 kilo-ohms).

The active damping circuit is generally preferred due to its ability to provide fast and consistent settling times. An active damping circuit added to the transmitter output can provide a low-impedance discharge path when the transmitter is disabled, while presenting a very high impedance while the transmitter is enabled. Unfortunately, the additional active damping circuit consumes substantial area in an ultrasound transmitter integrated circuit because the damping transistors are comparable in size to the high-voltage drive transistors. Embodiments of the present disclosure advantageously provide active damping without consuming additional circuit area.

FIG. 1 shows a block diagram of an exemplary ultrasound imaging system 100 in accordance with various embodiments. The terms "ultrasound" or "ultrasonic" generally refer to acoustic waves at frequencies beyond the range of human hearing (e.g., frequencies above 20 KHz). The system 100 comprises a transducer 102, a transmitter 104, a receiver 106, a signal processor 108, and a display 110. The transducer 102 converts the electrical drive signals generated by the transmitter 104 into sound waves (i.e., pressure waves) that are introduced into the subject to be imaged, for example, a human body when considering medical ultrasound. The transducer 102 can comprise a piezoelectric crystal, electromagnetic transducer, micro-electro-mechanical system ("MEMS") transducer or other device that converts an electrical signal into sound waves. Moreover, the transducer 102 can comprise one or more transducer elements. The transducer 102 also detects ultrasonic waves reflected by internal structures of the subject and converts the detected waves into electrical signals. In some embodiments, the same transducer elements are used to generate ultrasonic waves and to detect ultrasonic waves. In other embodiments, separate transducer elements are used for wave generation and detection.

The transmitter 104 is coupled to the transducer 102. The transmitter 104 produces an oscillating electrical signal at a frequency and amplitude suitable for imaging desired structures internal to the subject. For example, transmitter output signals for use in imaging the internal organs of a human body may range in frequency from 1 to 20 megahertz with lower frequencies providing lower resolution and greater imaging depth. Other applications may use different frequencies. The transmitter 104, while not limited to any particular signal amplitudes, may provide, for example, a drive signal amplitude in the range of +/−75 volts. Embodiments of the transmitter 104 of the present disclosure advantageously provide active damping of the transmitter output without employing dedicated damping circuitry. Thus, embodiments of the transmitter 104 reduce transmitter circuit area and correspondingly reduce transmitter circuit cost.

The receiver 106 is coupled to the transducer 102. As explained above, the transducer 102 detects ultrasonic waves reflected by subject internal structures. The transducer 102 converts the detected waves into electrical signals. The electrical signals are provided to the receiver 106. The receiver 106 performs initial processing of the received signals. Processing performed by the receiver 106 can include, for example, amplifying, filtering, digitizing, etc.

The signal processor 108 is coupled to the receiver 106. The signal processor 108 may, for example, provide post-digitization filtering of received signals, detect signal reflections, and prepare output signals for display on the display 110. The signal processor 108 may comprise, for example, a digital signal processor or other microprocessor or microcomputer and associated software programming along with attendant memory and interface devices, and/or dedicated hardware circuitry adapted to perform the processing functions. The display 110 may be a liquid crystal display, a cathode ray display, or any other suitable display device.

Figure 2:
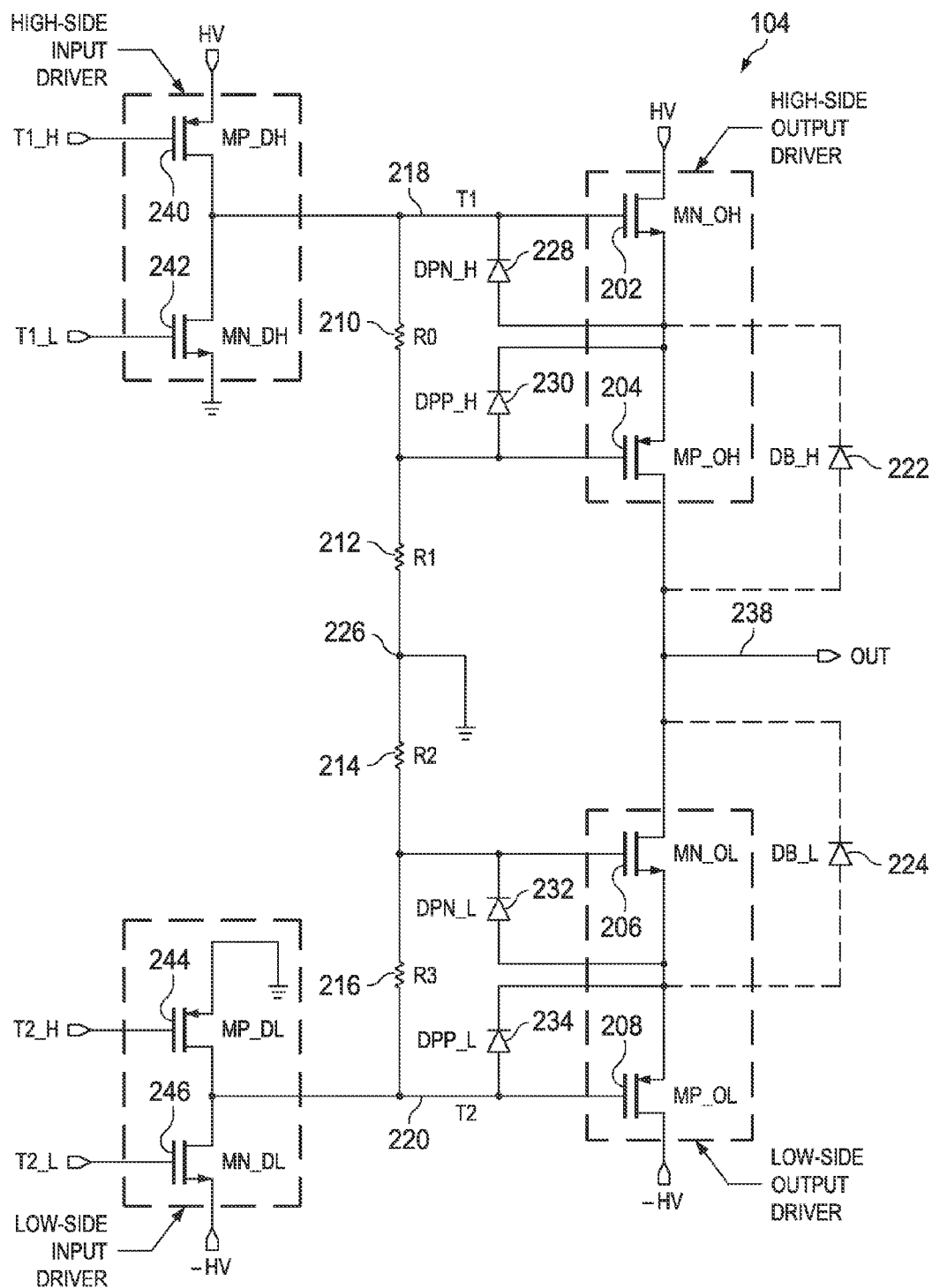
FIG. 2 shows an exemplary ultrasound transmitter circuit including a symmetrical output configuration and active damping of the transmitter output through the transmitter input drivers.

FIG. 2 shows an exemplary ultrasound transmitter circuit 104 including a symmetrical output configuration and active damping of the transmitter output through the transmitter input drivers. The transmitter 104 is configured to provide symmetry between the high side and the low side of the transmitter 104 output circuitry. Accordingly, the high-side driver and the low-side driver each include both a P-type transistor and an N-type transistor. The high-side driver comprises N-type transistor MN_OH 202 and P-type transistor MP_OH 204 connected in series. A diode 228 is connected between the gate and source of the N-type transistor MN_OH 202. A diode 230 is connected between the gate and source of the P-type transistor MP_OH 204. The low-side driver comprises N-type transistor MN_OL 206 and P-type transistor MP_OL 208 connected in series. A diode 232 is connected between the gate and source of the N-type transistor MN_OL 206. A diode 234 is connected between the gate and source of the P-type transistor MP_OL 208. When enabled, stacked drive transistors MN_OH 202 and MP_OH 204 provide high voltage, HV, to the transmitter output 238. Similarly, stacked drive transistors MN_OL 206 and MP_OL 208 provide high voltage, −HV, to the transmitter output 238 when enabled.

The stacked N-type and P-type transistors employed by embodiments of the present disclosure provide a number of advantages. Using an N-type transistor in series with a P-type transistor on both the high and low sides compensates for the lower mobility of the P-type transistor, and results in a smaller circuit area (for example, 15-20% less area) than would be required by an embodiment employing only P-type transistors on one side. Because the characteristics of one transistor type compensate for the characteristics of the other, high/low side symmetry also results in significantly improved performance in less than nominal conditions, for example, at temperature extremes or at process limits. Symmetry can provide a substantial improvement in the harmonic distortion present in the output signal. For example, at the process limits, symmetry can result in as much as a 25% reduction in the second harmonic content of the output with respect to the fundamental when compared to an asymmetrical embodiment.

Voltage should be predictably distributed across each transistor of a set of stacked transistors. The bias network comprising resistors R0 210, R1 212, R2 214, and R3 216 ensures that voltage is approximately equally distributed across each transistor of transistor pair MN_OH 202 and MP_OH 204, and each transistor of transistor pair MN_OL 206 and MP_OL 208 to assure that the breakdown voltage of the transistors is not exceeded. In some embodiments, for example, the voltage drop across a selected drive transistor may be within 10% of the voltage drop across the other drive transistor of the transistor pair.

In ultrasound applications, the duty cycle of the transmitter 104 can be low (i.e., the transmitter on time is short relative to the transmitter off time). For example, the transmitter 104 duty cycle may be in the range of 1% (i.e., on 1% of the time and off 99% of the time), so that even though the drive transistors 202, 204, 206, 208 may conduct a relatively large amount of current, the large amount of current is required for only a short period of time.

The high-side driver, comprising MN_OH 202 and MP_OH 204, is enabled to provide voltage HV to output 238 by asserting signal T1 218 (i.e., bringing the T1 218 signal voltage near HV). Similarly, the low side driver, comprising MN_OL 206 and MP_OL 208, is enabled to provide voltage −HV to output 238 by asserting signal T2 220 (i.e., bringing the T2 220 signal voltage near −HV). Either of the high-side or the low-side drivers can be disabled by bringing the corresponding control signal (T1 218 or T2 220) near to ground. Thus, when both the high and low side drivers are disabled, the voltages present on T1 218 and T2 220 are preferably approximately at ground. Consequently, the voltage drop across the bias network comprising R0 210, R1 212, R2 214, and R3 216 can be zero or very small when the transmitter 104 is disabled. By way of contrast, the current flowing in the bias network of a disabled asymmetrical output driver can be on the order of 10 milliamperes. Such a reduction in quiescent current is significant when the 1% duty cycle of the ultrasound transmitter 104 is considered.

The transmitter 104 includes a high-side input driver and a low-side input driver. The high and low side input drivers provide sufficient current to rapidly charge the gate capacitances of the output driver transistors MN_OH 202, MP_OH 204, MN_OL 206, MP_OL 208. The high-side input driver includes P-type transistor 240 and N-type transistor 242, and drives the high-side output driver control signal T1 218 to HV to enable the high-side output driver, and to ground to disable the high-side output driver. The low-side input driver includes P-type transistor 244 and N-type transistor 246, and drives the low-side output driver control signal T2 220 to −HV to enable the low-side output driver, and to ground to disable the low-side output driver. To disable the transmitter 104, both T1 218 and T2 220 are driven to ground.

FIG. 2 also shows the diode 222 across the high-side drive transistor MP_OH 204, and the diode 224 across the low-side drive transistor MN_OL 206. In some embodiments, the diodes 222, 224 are the body diodes associated with the respective drive transistors MP_OH 204 and MN_OL 206. To indicate their parasitic nature, the body diodes 222, 224 are shown connected via dashed lines.

The transmitter 104 is configured to allow the high and low side input drivers to operate as active damping circuits when the transmitter 104 is disabled (e.g., output drivers in a high-impedance state). When the transmitter 104 is to be transitioned from an active to inactive state, one of the high and low side driver circuits will be active and driving the output 238 to a high voltage. If, for example, the high-side driver is enabled, the output 238 is driven to HV. In this case, when T1 218 is driven to ground via the input driver transistor MN_DH 242, the high-side output driver is disabled, and a low impedance path is formed between the transmitter output 238 and ground. The low impedance path to ground is formed through the forward biased body diode 222, the forward biased gate protection diode 228, and the input driver transistor MN_DH 242. Via this path, the output 238 is quickly discharged and brought to ground potential.

Similarly, the low-side driver may be enabled and driving the output 238 to −HV prior to disabling the transmitter 104. When T2 220 is driven to ground via the input driver transistor MP_DL 244, the low-side output driver is disabled, and a low impedance path is formed between the transmitter output 238 and ground. The low impedance path to ground is formed through the forward biased body diode 224, the forward biased gate protection diode 234, and the input driver transistor MP_DL 244. Via this path, the output 238 is quickly discharged and brought to ground potential. Thus, embodiments provide active damping of the transmitter 104 output 238 without inclusion of a dedicated damping circuit.

An ultrasonic drive signal is generated by transmitter 104 as follows. MN_OH 202 and MP_OH 204 are turned on and MN_OL 206 and MP_OL 208 are turned off to drive the output 238 to +HV. MN_OH 202 and MP_OH 204 are turned off and MN_OL 206 and MP_OL 208 are turned on to drive the output 238 to −HV. Thus, the high and low side drivers are alternately turned on and off at the desired frequency to generate an ultrasonic drive signal on the transmitter output 238. During intervals when no ultrasonic drive signal is being generated, the high and low side drivers are disabled, and the transmitter output 238 returned to zero by bringing T1 218 and T2 220 to ground. In at least some embodiments, the output 238 is returned to zero for an interval between when one driver polarity is disabled and the other is enabled by disabling both drivers for the interval. In some embodiments, a single polarity output is generated by repetitively enabling and disabling a single polarity of driver. For example, by repetitively enabling and disabling MN_OH 202 and MP_OH 204, and holding MN_OL 206 and MP_OL 208 disabled, only positive voltage pulses are generated.

Figure 3:
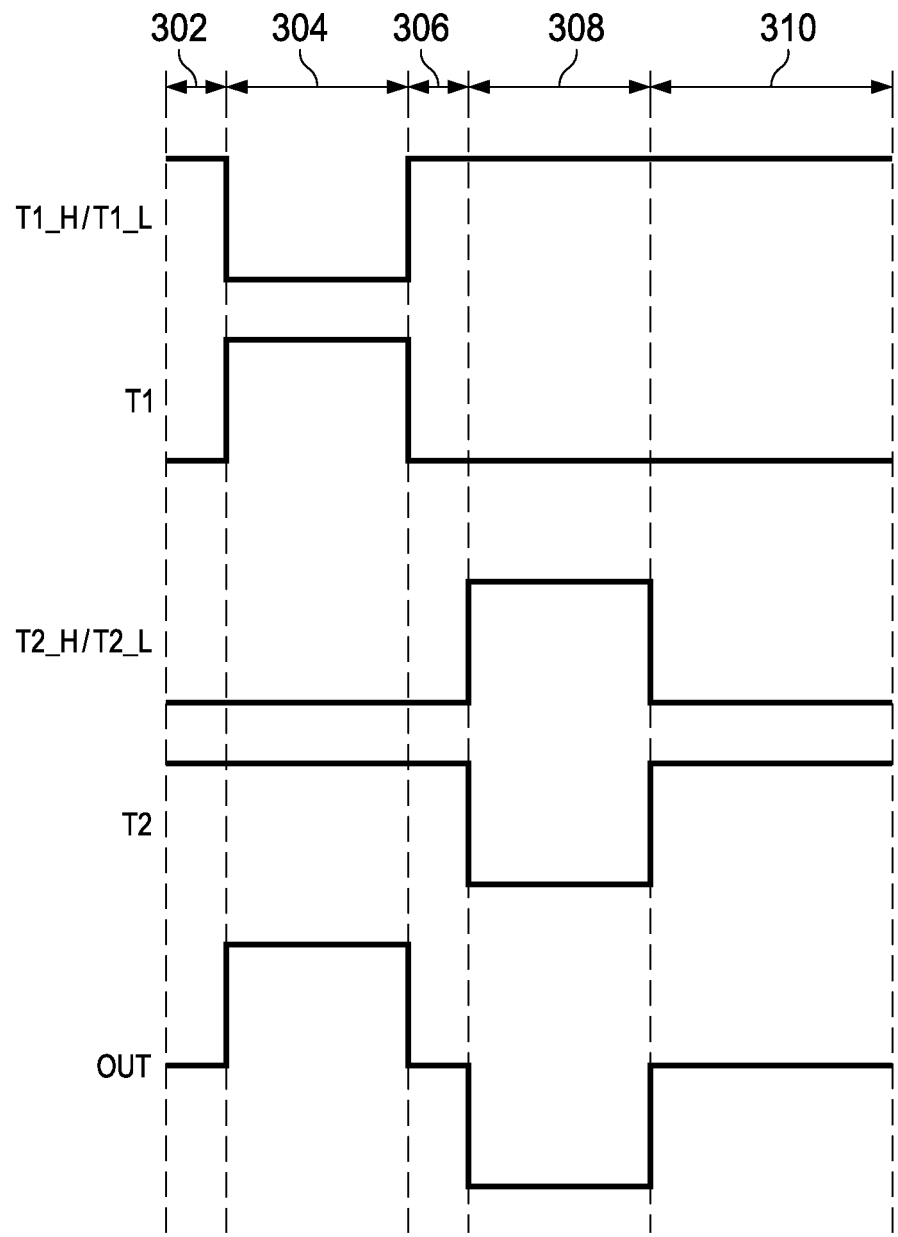
FIG. 3 shows a diagram of signals produced during operation of the ultrasound transmitter in accordance with various embodiments.

FIG. 3 shows a diagram of signals produced during operation of the ultrasound transmitter 104 in accordance with various embodiments The diagram begins, in period 302, with the high and low side transmitter output drivers disabled. The signals T1_H/T1_L and T2_H/T2_L are driven to cause the transmitter input drivers to drive T1 218 and T2 220 to ground, thereby disabling the transmitter output driver transistors.

In period 304, the signals T1_H/T1_L are asserted to cause the high-side transmitter input driver to drive T1 218 to HV, thereby enabling the high-side transmitter output driver transistors to drive the output 238 to HV. The output 238 is held at HV for a time period commensurate with the signal frequency to be generated. Thereafter, in period 306, the high-side transmitter output driver transistors are again disabled by asserting the signals T1_H/T1_L to drive T1 218 to ground. The period 306 may include zero or more time intervals. During period 306, the output 238 is discharged via the low impedance path formed by diodes 222 and 228, and input driver transistor 242.

In period 308, the signals T2_H/T2_L are driven to cause the low-side transmitter input driver to drive T2 220 to −HV, thereby enabling the low-side transmitter output driver transistors to drive the output 238 to −HV. The output 238 is held at −HV for a time period commensurate with the signal frequency to generated. Thereafter, in period 310, the low-side transmitter output driver transistors are again disabled by asserting the signals T2_H/T2_L to drive T2 220 to ground. The period 310 may include zero or more time intervals. During period 310, the output 238 is discharged via the low impedance path formed by diodes 224 and 234, and input driver transistor 244. A single cycle of transmitter 104 output signal is shown, however, embodiments may generate any number of successive output signal cycles.

Figure 4:
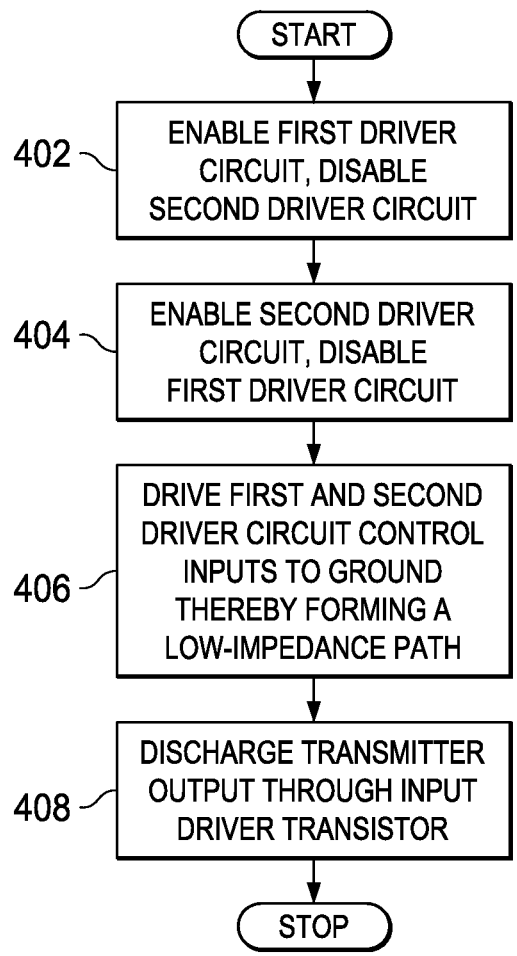
FIG. 4 shows a flow diagram for a method for operating a high voltage ultrasonic transmitter having automatic output damping in accordance with various embodiments.

FIG. 4 shows a flow diagram for a method for operating a high voltage ultrasonic transmitter having automatic output damping in accordance with various embodiments. Though depicted sequentially as a matter of convenience, at least some of the actions shown can be performed in a different order and/or performed in parallel. Additionally, some embodiments may perform only some of the actions shown.

Prior to block 402, the transmitter 104 is producing no ultrasonic drive signal. Consequently, the input driver transistors 242 and 244 are activated to drive the signals T1 218 and T2 220 to ground, turning off the transmitter output driver transistors MN_OH 202, MP_OH 204, MN_OL 206, and MP_OL 208.

In block 402, the transmitter 104 is generating a transducer drive signal. The input driver transistor 242 is disabled and the input driver transistor 240 is enabled to drive T1 218 to HV. In response to driving T1 218 to HV, the high-side output driver transistors MN_OH 202 and MP_OH 204 are enabled to drive HV to the transmitter output 238. The output 238 is maintained at HV in accordance with a desired output frequency.

In block 404, the high-side driver is disabled by bringing T1 218 to ground. T1 218 is driven to ground when the transistor MN_DH 242 of the input driver is enabled and transistor MP_DH 240 of the input driver is disabled.

The input driver transistor 244 is disabled and the input driver transistor 246 is enabled to drive T2 220 to −HV. In response to driving T2 220 to −HV, the low-side output driver transistors MN_OL 206 and MP_OL 208 are enabled to drive −HV to the transmitter output 238. The output 238 is maintained at −HV in accordance with a desired output frequency.

In block 406, both T1 218 and T2 220 are driven to ground by enabling input driver transistors 242 and 244 while disabling input driver transistors 240 and 246. A low-impedance path is formed between the transmitter output and ground.

In block 408, the transmitter output 238 discharges through the low impedance path formed by a body diode, a gate protection diode, and an input driver transistor to bring the transmitter output 238 to ground.

The above discussion is meant to be illustrative of the principles and various embodiments of the present invention. Numerous variations and modifications will become apparent to those skilled in the art once the above disclosure is fully appreciated. For example, embodiments describing an ultrasound transmitter have been described here. Those skilled in the art will recognize the embodiments of the transmitter described herein are not limited to ultrasound applications, but are applicable to a variety of applications where a transmitter includes output transistors having inputs driven to ground to disable the transmitter. It is intended that the following claims be interpreted to embrace all such variations and modifications.

What is claimed is:

1. A transmitter for generating ultrasound signals, comprising:
    an ultrasonic signal transducer that converts an electrical signal into an acoustical signal; and
    a first transmitter output driver comprising an N-type device serially coupled to a P-type device; and
    a first transmitter input driver comprising an N-type device serially coupled to a P-type device, an output of the first transmitter input driver being coupled to an input of the first transmitter output driver;
    wherein the first transmitter output driver, while enabled, drives an output of the transmitter to a first voltage, and the first transmitter input driver drives the output of the transmitter to a second voltage while the first transmitter output driver is disabled,
    a first diode connected to an input of the first transmitter output driver and the output of the first transmitter input driver;
    a second diode connected to the first diode and the output of the transmitter;
    wherein the first diode and the second diode form a path for current flow between the output of the transmitter and the first transmitter input driver when the transmitter output driver is disabled,
    a second transmitter output driver comprising an N-type device serially coupled to a P-type device; and
    a second transmitter input driver comprising an N-type device serially coupled to a P-type device, an output of the second transmitter input driver being coupled to the input of the second transmitter output driver;
    wherein the second transmitter output driver drives an output of the transmitter to a third voltage and the second transmitter input driver drives the output of the transmitter to the second voltage while the second transmitter output driver is disabled.

2. The transmitter of claim 1, wherein the first voltage is one of greater than 50 volts and more negative than −50 volts, and the second voltage is ground.

3. The transmitter of claim 1, wherein the first diode is connected to protect the gate of the N-type device of the first transmitter output driver from damaging voltages, and the second diode is a body diode of the P-type device of the first transmitter output driver.

4. The transmitter of claim 1, wherein disabling the transmitter comprises configuring the first and second transmitter input drivers to disable the first and second transmitter output drivers.

5. The transmitter of claim 1, further comprising:
    a third diode connected to an input of the second transmitter output driver and an output of the second transmitter input driver;
    a fourth diode connected to the third diode and the output of the transmitter;
    wherein the third diode and the fourth diode form a path for current flow between the output of the transmitter and the second transmitter input driver when the second transmitter output driver is disabled.

6. The transmitter of claim 5, wherein the third diode is connected to protect the gate of the P-type device of the second transmitter output driver from damaging voltages, and the fourth diode is a body diode of the N-type device of the second transmitter output driver.

7. The transmitter of claim 1, wherein disabling the transmitter comprises driving the gate input of the N-type device of the first transmitter output driver, and the gate input of the P-type device of the second transmitter output driver, to ground.

8. An ultrasound imaging system, comprising:
    an ultrasonic signal transducer that converts an electrical signal into an acoustical signal; and
    a signal transmitter coupled to the transducer, the signal transmitter comprising:
        a high-side output driver that drives a transmitter output to a first non-zero voltage when enabled; and
        a high-side input driver having an output coupled to control inputs of the high-side output driver, the high-side input driver being configured to selectively enable and disable the high-side output driver;
        wherein the high-side output driver, when disabled, provides a lower-impedance path from the transmitter output to the high-side input driver,
        wherein the low input path comprises a path through a forward biased body diode a forward biased gate protection diode and an input driver transistor,
    first diode connected to an input of the first transmitter output driver and the output of the first transmitter input driver;

a second diode connected to the first diode and the output of the transmitter;

wherein the first diode and the second diode form a path for current flow between the output of the transmitter and the first transmitter input driver when the transmitter output driver is disabled, a second transmitter output driver comprising an N-type device serially coupled to a P-type device; and a second transmitter input driver comprising an N-type device serially coupled to a P-type device, an output of the second transmitter input driver being coupled to the input of the second transmitter output driver;

wherein the second transmitter output driver drives an output of the transmitter to a third voltage and the second transmitter input driver drives the output of the transmitter to the second voltage while the second transmitter output driver is disabled.

9. The ultrasound imaging system of claim 8, wherein the high-side input driver provides a first lower-impedance path from the output of the transmitter to ground when the high-side output driver is disabled.

10. The ultrasound imaging system of claim 9, wherein the first lower-impedance path from the output of the transmitter to ground is formed through a body diode of a P-type drive transistor of the high-side output driver, an input protection diode connected to protect an N-type drive transistor of the high-side output driver, and an N-type drive transistor of the high-side input driver.

11. The ultrasound imaging system of claim 8, wherein the signal transmitter further comprises:

a low-side output driver that drives the transmitter output to a second non-zero voltage when enabled; and a low-side input driver having an output coupled to control inputs of the low-side output driver, the low-side input driver being configured to selectively enable and disable the low-side output driver;

wherein the low-side output driver, when disabled, provides a lower-impedance path from the transmitter output to the low-side input driver.

12. The ultrasound imaging system of claim 11, wherein the low-side input driver provides a second lower-impedance path from the output of the transmitter to ground when the low-side output driver is disabled.

13. The ultra-sound imaging system of claim 12, wherein the second lower-impedance path from the output of the transmitter to ground is formed through a body diode of an N-type drive transistor of the low-side output driver, an input protection diode connected to protect a P-type drive transistor of the low-side output driver, and a P-type drive transistor of the low-side input driver.

14. The ultrasound imaging system of claim 8, wherein high-side input driver disables the high-side output driver by driving a control input of each drive transistor of the high-side output driver to ground.

* * * * *